United States Patent [19]

Ago et al.

[11] Patent Number: 5,955,137
[45] Date of Patent: Sep. 21, 1999

[54] FERULIC ACID DECARBOXYLASE

[75] Inventors: Shoji Ago, Ami-machi; Yasuhiro Kikuchi, Tsukuba, both of Japan

[73] Assignee: Kyowa Hakko Kogyo Co., Ltd., Tokyo, Japan

[21] Appl. No.: 09/018,787

[22] Filed: Feb. 4, 1998

[30] Foreign Application Priority Data

Feb. 7, 1997 [JP] Japan .................................. 9-025026

[51] Int. Cl.⁶ ................................ C12G 2/40; C12P 7/06
[52] U.S. Cl. ............................................ 426/592; 435/161
[58] Field of Search ............................................ 426/592

[56] References Cited

PUBLICATIONS

Rosazza et al., "Review Biocatalytic Transformations of Ferulic Acid: An Abundant Aromatic Natural Product", Journal of Industrial Microbiology (1995) 15, pp. 457–471.
Hinnen et al., "Transformation of Yeast," Proc. Natl. Acad. Sci. USA, Apr. 1978, vol. 75, No. 4, pp. 1929–1933.
Clausen et al., "PAD1 Encodes Phenylacrylic Acid Decarboxylase," Gene, 142 (1994), pp. 107–112.
Huang et al., "Purification and Characterization of a Ferulic Acid Decarboxylase from *Pseudomonas Fluorescens*," Journal of Bacteriology, Oct. 1994, vol. 176, No. 19, pp. 5912–5918.

Lesage–Meessen et al., "A Two–Step Bioconversion Process for Vanillin Production," Journal of Biotechnology, 50 (1996) pp. 107–113.

Feron et al., "Prospects for the Microbial Production of Food Flavours," Trends in Food Science & Technology, Sep. 1996, vol. 7, pp. 285–293.

*Primary Examiner*—Robert A. Wax
*Attorney, Agent, or Firm*—Fitzpatrick, Cella, Harper & Scinto

[57] ABSTRACT

The present invention relates to a protein having the amino acid sequence represented by SEQ ID NO: 1, or a protein having ferulic acid decarboxylase activity and having an amino acid sequence wherein one or more amino acid residues are deleted, substituted or added in the amino acid sequence represented by SEQ ID NO: 1; a gene encoding said protein; a recombinant vector comprising said gene; a transformant carrying said recombinant vector; a process for producing 4-vinylguaiacol, vanillin or vanillic acid, or a distilled liquor, wherein an enzyme source having ferulic acid decarboxylase activity which is derived from said transformant is used; and a process for producing a distilled liquor, wherein yeast having an enhanced ferulic acid decarboxylase activity is used.

2 Claims, 2 Drawing Sheets

FERULIC ACID DECARBOXYLASE

BACKGROUND

1. Field of the Invention

The present invention relates to a process for producing distilled liquors having an excellent flavor by the use of yeast into which a ferulic acid decarboxylase gene has been introduced.

Ferulic acid decarboxylase is an enzyme which catalyzes the decarboxylation of ferulic acid to form 4-vinylguaiacol.

2. Brief Description of the Background Art

In the liquor industry, it is always desired to develop distilled liquors such as shochu (a Japanese distilled liquor), bai jiu (a Chinese distilled liquor), whiskey, brandy, vodka, rum, gin and the like having an excellent flavor. Distilled liquors possesing an excellent flavor typically have a relatively high content of at least one of 4-vinylguaiacol, vanillin, or vanillic acid.

Vanillin and vanillic acid are formed by oxidation of 4-vinylguaiacol [Nippon Nogeikagaku Kaishi, 70(6), 684–686 (1996)].

It is known that distilled liquors having an excellent flavor can be produced by adding hydroxycinnamic acid ester hydrolase, or a koji mold having a high productivity of hydroxycinnamic acid ester hydrolase, (Japanese Published Unexamined Patent Application No. 115957/95) or ferulic acid esterase [Nippon Nogeikagaku Kaishi, 70(6), 684–686 (1996)] to liberate ferulic acid into moromi.

Ferulic acid, as well as cinnamic acid and coumaric acid, is a kind of phenylacrylic acid, and is bonded in the form of ester to the arabinose side chain of arabinoxylan contained in the hemicellulose fraction which constitutes cell walls of plants such as cereals.

A method for preparing yeast having a high ferulic acid decarboxylase activity by cell fusion has been proposed [Abstracts of the Annual Meeting of the Society of Fermentation and Bioengineering, 41 (1995)]. However, it has not yet been possible to obtain yeast having an increased ferulic acid decarboxylase activity. Accordingly, a method of producing distilled liquors having an excellent flavor by the use of such yeast is not known.

Ferulic acid decarboxylase of *Bacillus pumilus* [Appl. Environ. Microbiol., 61(1), 326–332 (1995)] and that of *Pseudomonas fluorescens* [J. Bacteriol., 176, 5912–5918 (1994)] have already been isolated and purified. The gene encoding ferulic acid decarboxylase (hereinafter referred to as FDC gene) of *B. pumilus* [Appl. Environ. Microbiol., 61, 4484–4486 (1995)] is also known. Ferulic acid decarboxylase of yeast belonging to the genus Saccharomyces, etc. has not been isolated, even though the existence of the enzyme activity has been recognized.

As to *Saccharomyces cerevisiae*, the gene encoding phenylacrylic acid decarboxylase (hereinafter referred to as PAD1 gene) [Gene, 142, 107–112 (1994)] is known, but there is no report on its FDC gene.

An object of the present invention is to provide ferulic acid decarboxylase which is useful in the production of distilled liquors having an excellent flavor.

SUMMARY OF THE INVENTION

The present invention relates to a protein having the amino acid sequence represented by SEQ ID NO: 1, or a protein having ferulic acid decarboxylase activity and having an amino acid sequence wherein one or more amino acid residues are deleted, substituted or added in the amino acid sequence represented by SEQ ID NO: 1 (hereinafter referred to as the protein of the present invention); a gene encoding said protein (hereinafter referred to as the gene of the present invention); a recombinant vector comprising said gene (hereinafter referred to as the recombinant vector of the present invention); a transformant carrying said recombinant vector (hereinafter referred to as the transformant of the present invention); a process for producing 4-vinylguaiacol, vanillin, or vanillic acid, which comprises bringing ferulic acid into contact with an enzyme source having ferulic acid decarboxylase activity which is derived from said transformant in an aqueous medium to form 4-vinylguaiacol, vanillin, or vanillic acid in the aqueous medium, and recovering 4-vinylguaiacol, vanillin, or vanillic acid therefrom (hereinafter referred to as the process for producing 4-vinylguaiacol, vanillin, or vanillic acid of the present invention); a process for producing a distilled liquor, which comprises adding an enzyme source having ferulic acid decarboxylase activity which is derived from said transformant to moromi (hereinafter referred to as the process for producing a distilled liquor by using the protein of the present invention); and a process for producing a distilled liquor, which is characterized in that yeast having an enhanced ferulic acid decarboxylase activity is used (hereinafter referred to as the process for producing a distilled liquor by using the yeast of the present invention).

The present invention provides a distilled liquor produced by the above-mentioned processes for producing a distilled liquor.

DETAILED DESCRIPTION OF THE INVENTION

Figure 1:
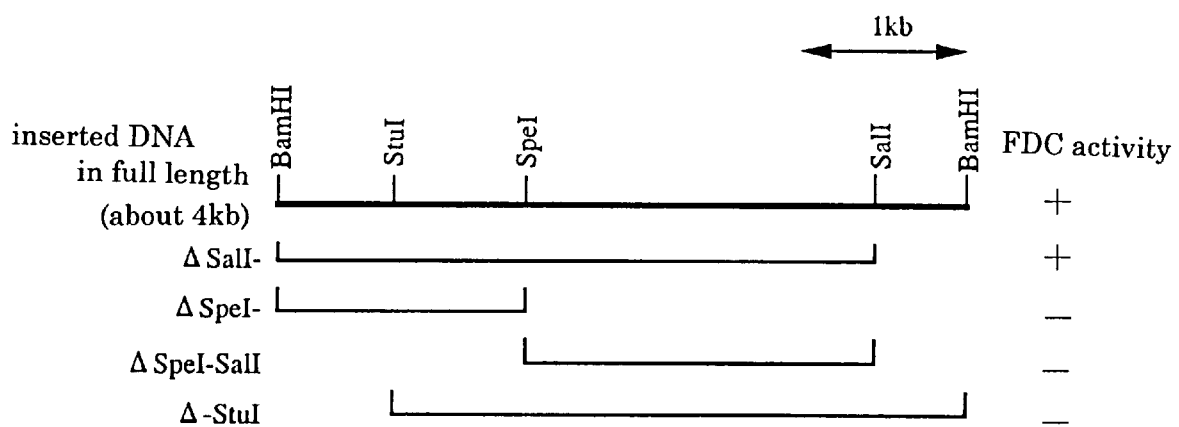
FIG. 1 shows the restriction map of the DNA fragment containing Saccharomyces FDC1 gene and the result of the subcloning carried out for the determination of FDC1 gene as well as the FDC activity of the obtained DNA fragments.

The protein of the present invention can be a protein having an amino acid sequence wherein amino acid residues are deleted, substituted or added in the amino acid sequence represented by SEQ ID NO: 1 so long as it has ferulic acid decarboxylase activity, i.e. the activity of catalyzing decarboxylation of ferulic acid to form 4-vinylguaiacol. The number of amino acid residues which are deleted, substituted or added is not specifically limited, but as is well-known to those of ordinary skill in the art, is normally within the range of one to several tens, preferably one to ten or fewer. Preferred amino acid sequences are those showing 20% or more homology, particularly 40% or more homology to the amino acid sequence represented by SEQ ID NO: 1 on simple homology analysis on the entire sequence using DNASIS version 3.0 (Hitachi Software Engineering Co., Ltd.).

Isolation of the gene of the present invention, determination of the nucleotide sequence of said gene, by preparation of the recombinant vector of the present invention and the transformant carrying the recombinant vector of the present invention, and production of the protein of the present invention can be carried out given the information provided herein by those of ordinary skill in this art using basic techniques for genetic engineering and biological engineering according to the descriptions in commercially available experiment manuals, e.g. Gene Manual, Kodansha Co., Ltd.; Methods for Experiments in Gene Manipulation, edited by Yasutaka Takagi, Kodansha Co., Ltd.; Molecular Cloning, Cold Spring Harbor Laboratory (1982); Molecular Cloning, 2nd ed., Cold Spring Harbor Laboratory (1989); Methods in Enzymol., 194 (1991); and Gene Experiments Using Yeasts, published by Yodosha Co., Ltd., Japan (1994).

The gene of the present invention conferring ferulic acid decarboxylase activity can be isolated using yeast having no ferulic acid decarboxylase activity or yeast having a very low ferulic acid decarboxylase activity (hereinafter collectively referred to as yeast having substantially no ferulic acid decarboxylase activity), e.g. *Saccharomyces cerevisiae* K9H14 (hereinafter referred to as K9H14 strain). That is, the FDC gene can be isolated by transforming K9H14 strain with the DNA library of the yeast carrying FDC gene, and obtaining DNA from transformed yeast conferred with ferulic acid decarboxylase activity.

The DNA library of the yeast carrying FDC gene can be prepared by cleaving the chromosomal DNA of yeast having ferulic acid decarboxylase activity, e.g. *Saccharomyces cerevisiae* W3 (hereinafter referred to as W3 strain), which is wine yeast, with a restriction enzyme, and ligating each of the obtained DNA fragments with a vector capable of being maintained in yeast.

Any restriction enzyme which can cleave the chromosomal DNA can be used in the above process. Preferably, those which give DNA fragments of 10 Kbp or less are used. The chromosomal DNA may be completely digested or partially digested with the restriction enzyme.

Examples of the vectors capable of being maintained in yeast are YCp vectors, YEp vectors, YRp vectors, YIp vectors, and YAC (yeast artificial chromosome) vectors.

The transformation of K9H14 strain with the DNA library can be carried out according to the methods generally used in genetic engineering and biological engineering such as the spheroplast method [e.g. Proc. Natl. Acad. Sci. USA, 75, 1929–1933 (1978)], the lithium acetate method [e.g. J. Bacteriol., 153, 163–168 (1983)], and the electroporation method [e.g. Methods in Enzymol., 194, 182–187 (1991)].

The yeast conferred with ferulic acid decarboxylase activity can be selected, for example, in the following manner.

The transformants obtained by the above process are cultured overnight (20–24 hours) in YPD liquid medium (1% yeast extract, 2% peptone, and 2% glucose). To 0.9 ml of each of the resulting cultures is added 0.1 ml of 1 g/l ferulic acid solution, followed by culturing for 20–24 hours. After the completion of culturing, the cultures having a smoky smell are selected organoleptically, followed by high performance liquid chromatography [Nippon Nogeikagaku Kaishi, 69, 1587–1596 (1995)] to further select the cultures from which 4-vinylguaiacol can be detected. Transformants are isolated from the thus selected cultures, whereby the yeasts conferred with ferulic acid decarboxylase activity are selected.

As the ferulic acid, either trans-ferulic acid or cis-ferulic acid may be used. However, trans-ferulic acid is preferably used.

Recovery of a plasmid from the yeast conferred with ferulic acid decarboxylase activity and transformation of *Escherichia coli* using the plasmid can be carried out according to the methods generally used in genetic engineering. For example, the plasmid can be recovered from the yeast by the method described in Gene Experiments Using Yeasts (an extra number of Experimental Medicine), Yodosha Co., Ltd. (1994), and the transformation can be carried out by the method described in Molecular Cloning, 2nd ed., Cold Spring Harbor Laboratory (1989).

The DNA clone selected by the above method is cleaved with appropriate restriction enzymes and the obtained DNA fragments are subjected to nucleotide sequence analysis by using the dideoxy method, etc., whereby the nucleotide sequence of FDC gene can be determined. The nucleotide sequence of FDC gene derived from W3 strain can be obtained from the result of the yeast genome project [e.g. Internet http://genome-www. stanford. edu/sacchdb/].

An example of the nucleotide sequence of FDC gene determined in such manner is the sequence represented by SEQ ID NO: 1.

Once it is established that the nucleotide sequence represented by SEQ ID NO: 1 encodes ferulic acid decarboxylase, the gene of the present invention can be obtained by chemical synthesis, PCR (polymerase chain reaction), or hybridization using a DNA fragment having said nucleotide sequence as a probe.

The gene of the present invention includes modified genes obtained by artificial deletion, substitution or addition of a part of the nucleotide sequence of the gene prepared by the above-described method. Selection of a codon for each amino acid can be made on arbitrary basis, for example, by referring to the codon usage of a host to be employed [e.g. Nucleic Acids Res., 9, 43–74 (1981)].

It is preferred to appropriately substitute bases in the nucleotide sequence of the gene of the present invention used for the preparation of the recombinant vector, so as to give the codons most suitable for the expression of the gene in a host cell. Modification of the nucleotide sequence can also be carried out according to the methods such as site-specific mutagenesis [e.g. Proc. Natl. Acad. Sci. USA, 81, 5662–5666 (1984)].

Gene disruption, regulation of expression, and alteration of expression level can be effected on the gene a of the present invention by using, for example, the methods described in Methods in Enzymol., 194, 594–597 (1991).

The recombinant vector of the present invention can be obtained by preparing a DNA fragment comprising the gene of the present invention by using restriction enzymes, etc., and inserting the DNA fragment into an expression vector at an insertion site located downstream of the promoter therein. The transformant of the present invention can be obtained by introducing the recombinant vector of the present invention into a host cell suited to the above-mentioned expression vector.

In the recombinant vector of the present invention, the transcription termination sequence is not essential for the expression of the gene of the present invention, but it is preferred that the transcription termination sequence be located immediately downstream of the structural gene.

As the host cells, any cells capable of expressing the above gene can be used. Examples of suitable host cells are cells of bacteria belonging to the genus Escherichia, Serratia, Corynebacterium, Brevibacterium, Pseudomonas, or Bacillus (e.g. *Escherichia coli, Bacillus subtilis, Bacillus amyloliquefaciens, Brevibacterium flavum, Brevibacterium lactofermentum, Corynebacterium glutamicum,* and *Microbacterium ammoniaphilum*), cells of yeasts such as *Saccharomyces cerevisiae, Schizosaccharomyces pombe, Kluyveroymces lactis, Trichosporon pullulans,* and *Schwanniomyces alluvius,* animal cells such as Namalwa cell, COS cell and CHO cell, and plant cells such as tobacco cell and carrot cell.

As the expression vector, vectors capable of autonomous replication or integration into chromosome in the above cells and comprising a promoter at a site appropriate for the transcription of the nucleotide sequence of the gene of the present invention are used.

When bacterial cells such as E. coli are used as the host cells, it is preferred to use the recombinant vector of the present invention which is capable of autonomous replication in the cells used and which comprises a promoter, a ribosome binding sequence, the DNA of the present invention, and a transcription termination sequence. The vector may further comprise a gene regulating the promoter.

Examples of suitable expression vectors are pBTrp2, pBTac1 and pBTac2 (products of Boehringer Mannheim), pKYP200 [Agric. Biol. Chem., 48, 669–675 (1984)], pLSA1 [Agric. Biol. Chem., 53, 277 (1989)], pGEL1 [Proc. Natl. Acad. Sci. USA, 82, 4306 (1985)], and pBluescript (product of Stratagene).

As the promoter, any promoters capable of expression in host cells such as E. coli can be used. For example, promoters derived from E. coli or phage, such as trp promoter (Ptrp), lac promoter (Plac), $P_L$ promoter, and $P_R$ promoter, may be used. Artificially modified promoters such as a promoter in which two Ptrps are combined in tandem (Ptrp×2) and tac promoter can also be used.

As the ribosome binding sequence, any ribosome binding sequences capable of expression in host cells such as E. coli can be used. It is preferred to adjust the distance between the ribosome binding sequence and the initiation codon to appropriate length (e.g. 6–18 bases).

Introduction of the recombinant vector into bacterial cells can be carried out by any of the methods for introducing DNA into bacterial cells, for example, the method using calcium ion [Proc. Natl. Acad. Sci. USA, 69, 2110–2114 (1972)] and the protoplast method (Japanese Published Unexamined Patent Application No. 2483942/88).

When yeast cells are used as the host cells, YEp13 (ATCC 37115), YEp24 (ATCC 37051), YCp50 (ATCC 37419), etc. can be used as the expression vector.

As the promoter, any promoters capable of expression in yeast cells can be used. Examples of suitable promoters are promoters of genes in the glycolytic pathway such as hexose kinase, gal 1 promoter, gal 10 promoter, heat shock protein promoter, MFα11 promoter, and CUP 1 promoter.

Introduction of the recombinant vector into yeast cells can be carried out by any of the methods for introducing DNA into yeast cells, for example, the electroporation method [Methods in Enzymol., 194, 182–187 (1990)], the spheroplast method [Proc. Natl. Acad. Sci. USA, 84, 1929–1933 (1978)], and the lithium acetate method [J. Bacteriol., 153, 163–168 (1983)].

When animal cells are used as the host cells, pcDNAI/Amp, pcDNAI and pcDM8 (products of Funakoshi Co., Japan), etc. can be used as the expression vector. As the promoter, any promoters capable of expression in animal cells can be used. An example of a suitable promoter is the promoter of IE (immediate early) gene of human CMV. The enhancer of IE gene of human CMV may be used in combination with the promoter.

Introduction of the recombinant vector into animal cells can be carried out by any of the methods for introducing DNA into animal cells, for example, the electroporation method [Cytotechnology, 3, 133 (1990)], the calcium phosphate method (Japanese Published Unexamined Patent Application No. 227075/90), and the lipofection method [Proc. Natl. Acad. Sci. USA, 84, 7413 (1987)].

When plant cells are used as the host cells, pBI121 [Nucleic Acids Res., 12, 8771–8721 (1984)], etc. can be used as the expression vector. As the promoter, any promoters capable of expression in plant cells can be used. An example of a suitable promoter is 35S promoter of cauliflower mosaic virus.

Introduction of the recombinant vector into plant cells can be carried out by any of the methods for introducing DNA into plant cells, for example, the Agrobacterium tumefaciens method [Methods in Enzymol., 118, 627–640 (1986)], the particle bombardment method [Plant Molecular Biology, 11, 433–439 (1989)], and the protoplast method [Nature, 319, 791–793 (1986)].

The transformant of the present invention is used for the production of the protein of the present invention and production of flavors such as 4-vinylguaiacol, vanillin and vanillic acid. Further, the transformant of the present invention prepared by using yeast cells as the host cells is preferably used for the production of distilled liquors having an excellent flavor.

The protein of the present invention can be produced by culturing the transformant of the present invention in a medium, allowing the protein of the present invention to accumulate in the culture, and recovering the protein from the culture. Culturing of the transformant of the present invention can be carried out by conventional methods for culturing the host cells of the transformant.

For the culturing of the transformant prepared by using microbial cells such as E. coli cells and yeast cells as the host cells, either a natural medium or a synthetic medium may be used insofar as it is a medium suitable for efficient culturing of the transformant which contains carbon sources, nitrogen sources, inorganic salts, etc. which can be assimilated by the microorganism used.

Examples of the carbon sources for microbial cells include carbohydrates such as glucose, fructose, sucrose, molasses, starch and starch hydrolyzate; organic acids such as acetic acid and propionic acid; and alcohols such as ethanol and propanol.

As the nitrogen sources for microbial cells, ammonia, ammonium salts of inorganic or organic acids such as ammonium chloride, ammonium sulfate, ammonium acetate and ammonium phosphate, and other nitrogen-containing compounds can be used as well as peptone, meat extract, yeast extract, corn steep liquor, casein hydrolyzate, soybean cake, soybean cake hydrolyzate, and various fermented cells and digested products thereof.

Examples of the inorganic substances for microbial cells include potassium monohydrogenphosphate, potassium dihydrogenphosphate, magnesium phosphate, magnesium sulfate, sodium chloride, ferrous sulfate, manganese sulfate, copper sulfate and calcium carbonate.

Culturing of transformed microbial cells is usually carried out under aerobic conditions, for example, by shaking culture or submerged aeration stirring culture, at 15–40° C. for 16–96 hours. The pH is maintained at 3.0–9.0 during the culturing. If necessary, antibiotics such as ampicillin and tetracycline may be added to the medium.

When a microorganism transformed with an expression vector comprising an inducible promoter is cultured, an inducer may be added to the medium, if necessary. For example, in the case of a microorganism transformed with an expression vector comprising lac promoter, isopropyl-β-D-thiogalactopyranoside (IPTG) or the like may be added to the medium; and in the case of a microorganism transformed with an expression vector comprising trp promoter, indole-acrylic acid (IAA) or the like may be added.

For the culturing of the transformant prepared by using animal cells as the host cells, either a natural medium or a synthetic medium may be used insofar as it is a medium suitable for efficient culturing of the transformant which contains carbon sources, nitrogen sources, inorganic salts, etc. which can be assimilated by the animal cells. Examples of suitable media are RPMI1640 medium, Eagle's MEM medium, and media prepared by adding fetal calf serum, etc. to these media.

Culturing of microbial cells is usually carried out in the presence of 5% $CO_2$ at 35–37° C. for 3–7 days. If necessary, antibiotics such as kanamycin and penicillin may be added to the medium.

For the culturing of the transformant prepared by using plant cells as the host cells, either a natural medium or a synthetic medium may be used insofar as it is a medium suitable for efficient culturing of the transformant which contains carbon sources, nitrogen sources, inorganic salts, etc. which can be assimilated by the plant cells. Examples of suitable media are Murashige-Skoog (MS) medium and White medium.

Culturing of plant cells is usually carried out under aerobic conditions, for example, by shaking culture or submerged aeration stirring culture, at 15–40° C. for 1–30 days. The pH is maintained at 3.0–9.0 during the culturing. If necessary, antibiotics such as kanamycin and penicillin may be added to the medium.

After the completion of culturing, the protein of the present invention produced inside or outside the cells of the transformant of the present invention can be isolated and purified according to ordinary methods for the isolation and purification of enzymes. When the protein is intracellularly produced, the isolation and purification can be carried out in the following manner. The cells are separated from the culture by centrifugation and washed, followed by disruption using an ultrasonic disrupter, a French press, a Manton Gaulin homogenizer, a Dyno Mill, etc. to obtain a cell-free extract. The cell-free extract is centrifuged, and the obtained supernatant is subjected to salting-out with ammonium sulfate, etc., anion exchange chromatography using diethylaminoethyl (DEAE)-Sepharose, etc., hydrophobic chromatography using butyl Sepharose, phenyl Sepharose, etc., gel filtration using a molecular sieve, electrophoresis such as isoelectric focusing, etc., whereby a purified enzyme preparation of the protein of the present invention is obtained. When the protein is extracellularly produced, the culture is treated in the same manner as in the above treatment of the cell-free extract to obtain a purified enzyme preparation of the protein of the present invention.

The enzyme source having ferulic acid decarboxylase activity which is derived from the transformant of the present invention to be used in the process for producing 4-vinylguaiacol, vanillin, or vanillic acid of the present invention includes the partially or highly purified protein of the present invention obtained by the above-described method, as well as culture, cells and treated cells of the transformant of the present invention. Examples of the treated cells include cells which are physicochemically or biochemically treated such as washed cells, lyophilized cells and acetone-treated cells.

The enzyme source is usually used at a concentration of 0.1–1000 units ferulic acid decarboxylase/ml aqueous medium. The amount of ferulic acid decarboxylase is expressed in terms of a unit, one unit being defined as that amount of the enzyme which produces 1 nmol of 4-vinylguaiacol by the reaction using ferulic acid as the substrate in 50 mM phosphate buffer (pH 5.0) at 30° C. for one hour. Ferulic acid is usually used at a concentration of 0.01–10 g/l in an aqueous medium.

When the culture or cells are used as the enzyme source, the culture or cell suspension may be treated with a surfactant such as cetylpyridinium chloride or cetyltrimethylammonium bromide, or an organic solvent such as toluene or xylene. The surfactant or organic solvent is added in an amount of 0.05–1.0% (w/v) or 1–20% (v/v), respectively.

The reaction is usually carried out at 20–60° C. at pH 2.5–10.0 for 1–72 hours, though these conditions are varied according to the amount of culture, cells or treated cells and the amount of ferulic acid.

By the above reaction, 4-vinylguaiacol is formed in the aqueous medium. After the completion of reaction, the culture, cells, treated cells, etc. are disrupted, if necessary. Then, the precipitate is removed from the aqueous medium by means such as centrifugation, and the obtained supernatant is subjected to ordinary purification steps such as extraction, distillation, various kinds of chromatography, and recrystallization, whereby 4-vinylguaiacol can be isolated and purified.

Vanillin or vanillic acid can be obtained by oxidizing 4-vinylguaiacol in the aqueous medium, or 4-vinylguaiacol can be isolated and purified from the aqueous medium by means such as forced aeration or by the use of cells of microorganisms such as *Bacillus subtilis* and *Corynebacterium glutamicum* [J. Ind. Microbiol., 15, 457–471 (1995)].

Isolation and purification of vanillin or vanillic acid can be carried out in the same manner as in the isolation and purification of 4-vinylguaiacol.

According to the process for producing a distilled liquor by using the protein of the present invention, a distilled liquor can be obtained in the same manner as in a conventional process for producing a distilled liquor which comprises saccharification of a carbon source with a koji mold or a sacchariferous enzyme, alcohol fermentation caused by addition of yeast, and distillation, except that the enzyme source having ferulic acid decarboxylase activity which is derived from the transformant of the present invention is added to moromi at a concentration of 0.1–50 units/ml as the amount of ferulic acid decarboxylase. The moromi means a culture obtained through alcohol fermentation. The distilled liquor means an alcoholic liquor obtained by distillation of the moromi as such, or the moromi after treatment with the pressure filtration or centrifugation.

According to the process for producing a distilled liquor by using the yeast of the present invention, a distilled liquor can be obtained in the same manner as in a conventional process for producing a distilled liquor which comprises saccharification of a carbon source with a koji mold or a sacchariferous enzyme, alcohol fermentation caused by addition of yeast, and distillation, except that yeast having an enhanced ferulic acid decarboxylase activity is used.

The term "yeast having an enhanced ferulic acid decarboxylase activity" means yeast which is obtained through recombinant DNA techniques or mutation techniques using a yeast strain as host cells or parent strain and which has ferulic acid decarboxylase activity higher than that of the yeast strain used as the host cells or parent strain.

For example, the yeast having an enhanced ferulic acid decarboxylase activity can be prepared by recombinant DNA techniques in the following manner. A recombinant vector comprising a gene encoding ferulic acid decarboxylase (e.g. the gene of the present invention, and FDC gene of *Bacillus pumilus*) is prepared by the above method, and host cells are transformed with the recombinant vector by the above method, whereby the desired yeast can be obtained.

The yeast having an enhanced ferulic acid decarboxylase activity can also be prepared by mutation techniques in the following manner. A parent strain is subjected to mutation treatment by conventional methods, for example, ultraviolet irradiation and treatment with mutagens such as ethyl methanesulfonate and N-methyl-N'-nitro-N-nitrosoguanidine. From the obtained mutants is selected a strain having an enhanced 4-vinylguaiacol productivity compared with the parent strain by the same method as in the above-described selection of the yeast conferred with ferulic acid decarboxylase activity, whereby the desired yeast can be obtained. Further, the yeast having an enhanced ferulic acid decarboxylase activity can be efficiently produced by culturing the mutants obtained as above on a medium containing phenylacrylic acid at such a concentration that the parent strain cannot grow sufficiently, for example, a medium containing 1 mM or more ferulic acid, and then selecting a mutant which shows significant growth compared with the parent strain.

Any yeast which is suitable for use in the production of distilled liquors can be used as the host cells or parent strain for preparing the yeast having an enhanced ferulic acid decarboxylase activity. Preferably, yeasts belonging to the genus Saccharomyces are used, and more preferably, those belonging to *Saccharomyces cerevisiae* are used. In particular, the use of yeasts belonging to *Saccharomyces cerevisiae* which have substantially no ferulic acid decarboxylase activity, e.g. yeast No. 7 of Japan Brewing Association, yeast No. 9 of Japan Brewing Association and K9H14 strain (sake and shochu yeasts), and IFO2112, IFO2114 and IFO2115 (whiskey yeasts), as the host cells gives a remarkable effect.

The yeast of the present invention can be prepared using yeast having substantially no ferulic acid decarboxylase activity as the host cells in the following manner. Transformants are prepared by the method similar to that for preparing the transformant of the present invention, and ferulic acid is added thereto as the substrate. Detection of 4-vinylguaiacol is carried out organoleptically, or quantitatively by means of high performance liquid chromatography, etc. to select the strains with which the formation of 4-vinylguaiacol is confirmed, whereby the desired yeast can be obtained.

An example of the yeast of the present invention prepared by the above method is *Saccharomyces cerevisiae* YSA7 (hereinafter referred to as YSA7 strain). This strain was deposited with the National Institute of Bioscience and Human-Technology, Agency of Industrial Science and Technology, Ministry of International Trade and Industry (1-3, Higashi 1-chome, Tsukuba-shi, Ibaraki-ken, Japan) on Dec. 11, 1996 with accession number FERM BP-5772 under the Budapest Treaty.

The following Test Example shows that YSA7 strain is yeast having an enhanced ferulic acid decarboxylase activity.

TEST EXAMPLE 1

Ferulic Acid Decarboxylase Activity Test

The test was carried out on YSA7 strain, K9H14 strain (parent strain of YSA7 strain), and K9H14-C strain (transformant prepared by introducing YEp24 into K9H14 strain). One loopful of each strain was inoculated into 10 ml of YPD medium in a test tube, and cultured with shaking at 30° C. for 22 hours. To 0.9 ml of the resulting culture was added 0.1 ml of 1 g/l ferulic acid solution, followed by static culture at 25° C. for 22 hours. After the completion of culturing, the 4-vinylguaiacol content of the culture supernatant was determined by high performance liquid chromatography under the following conditions.

Column: Wakosil 5C 18–200 (i.d. 4.6×250 mm)
Column temperature: 50° C.
Mobile phase: 10 mM phosphate buffer (pH 2.5)/methanol= 50/50 (v/v)
Detector: Fluorescence detector (Ex 280 nm, Em 320 nm)
Sample: The culture supernatant was diluted 10-fold with the mobile phase and 10 μl of the dilution was put into the column.

The results are shown in Table 1.

TABLE 1

| Strain | Amount of 4-vinylguaiacol formed (ppm) |
| --- | --- |
| YSA7 strain | 4.88 |
| K9H14 strain | Trace |
| K9H14-C strain | Trace |

The process for producing a distilled liquor of the present invention using the yeast having an enhanced ferulic acid decarboxylase activity which is prepared by the above method is described below.

As the carbon source, any non-fibrous carbohydrates and starch can be used. Preferred carbon sources are cereals such as rice, barley, foxtail millet, corn, kaoliang, Japanese millet and millet, potatoes, buckwheat, fruits such as grapes and apples, and koji thereof. Particularly preferred are cereals and koji thereof.

As the koji mold, filamentous fungi used for preparing rice koji, barley koji, bran koji, etc., e.g. microorganisms belonging to the genus Aspergillus or Rhizopus may be used. The koji means carbon sources molded with the above-mentioned koji mold.

As the sacchariferous enzyme, enzymes contained in malt, enzymes produced by koji mold, enzyme preparations such as α-amylase, gluco amylase and protease, etc. may be used.

Alcohol fermentation can be carried out, for example, in the following manner. When cereals are used, fermentation is carried out by parallel complex fermentation in which the cereals, which are starch, are decomposed to saccharides with a sacchariferous enzyme and then the yeast is added to cause fermentation. For example, in the production of shochu, the materials are generally added stepwise by first addition and second addition; that is, koji is added at the start of fermentation, and in the course of fermentation, the remaining part of the carbon source is added. For the production of whiskey, a method is generally employed in which malt is saccharified by addition of warm water and the obtained mash is fermented. When non-fibrous carbohydrates such as fruits, molasses and glucose are used, fermentation is carried out by single fermentation in which the yeast is directly added to the carbon source to cause fermentation.

Usually, the alcohol fermentation is carried out at pH 3.5–5.0 at a temperature of 5–25° C., and the fermentation period after the addition of materials is 7–14 days for shochu, 3–4 days for whiskey, and 7–14 days for brandy.

After the completion of alcohol fermentation, if necessary, the obtained moromi is subjected to pressure filtration or centrifugation to remove the fermentation residue and the yeast cells. The moromi as such or the resulting filtrate or supernatant is distilled to raise the ethanol concentration, whereby a raw liquor is obtained. Alternatively, alcohol may be added to the moromi before pressure filtration or centrifugation to obtain a raw liquor. The raw liquor is directly, or after treatment such as blending, dilution, and addition of alcohol, made into the form of an alcoholic beverage.

Certain embodiments of the invention are illustrated in the following Examples.

Example 1

Cloning of the Gene Encoding Ferulic Acid Decarboxylase (1) Conferment of ura3 mutation on K9H14 strain K9H14 strain, which is a monoploid strain of *Saccharomyces cerevisiae* No. 9 of Japan Brewing Association [a sake (shochu) yeast of Japan Brewing Association] and which has substantially no ferulic acid decarboxylase activity, was conferred with ura3 mutation as a marker for introducing a plasmid according to the method of Boeke, et al. [Mol. Gen. Genet., 197, 345–346 (1984)]. That is, one loopful of K9H14 strain was inoculated into YPD medium and cultured overnight at 30° C. with shaking. The resulting culture (100 μl) was smeared on FOA plate [0.67% Yeast Nitrogen Base w/o Amino Acid (Difco Laboratories Inc.), 0.1% 5-fluoroorotic acid, 0.005% uracil, 2% glucose, and 2% agar], and cultured at 30° C. for 3 days. From the colonies formed by the culturing was selected a strain having uracil-requirement which is complemented by transformation with plasmid YCp50 carrying URA3 as a marker, and having no ferulic acid decarboxylase activity. This strain was designated K9H14-3u strain. K9H14-3u strain was equal to K9H14 strain in properties such as fermentability.

(2) Cloning

The chromosomal DNA of W3 strain (wine yeast) was partially digested with BamHI, and the obtained DNA fragments were inserted into the BamHI site of plasmid YCp50 to prepare the gene library. K9H14-3u strain was transformed with the gene library, followed by selection of non-uracil-requiring transformants. The obtained transformants were cultured overnight in YPD liquid medium at 30° C. with shaking. To 0.9 ml of each of the resulting cultures was added 0.1 ml of 1 g/l ferulic acid solution, followed by static culture at 25° C. for 22 hours. After the completion of culturing, the cultures having a strong smoky smell were selected organoleptically, and the culture supernatants were subjected to high performance liquid chromatography, whereby the formation of 4-vinylguaiacol was confirmed.

A strain obtained from one of the thus selected cultures was isolated as a strain conferred with ferulic acid decarboxylase activity. From this strain was extracted recombinant plasmid pSA11.

Plasmid pSA11 carried an inserted BamHI-BamHI fragment of about 4 kbp. This plasmid was cleaved with various restriction enzymes and the obtained DNA fragments were separated by electrophoresis, followed by measurement of molecular weights, to prepare the restriction map as shown in FIG. 1.

(3) Determination of nucleotide sequence

The nucleotide sequence of the 4 kbp BamHI-BamHI DNA fragment inserted into plasmid pSA11 was determined by the dideoxy method using a DNA sequencer (Pharmacia LKB, ALF DNA Sequencer II). As a result, the nucleotide sequence shown by SEQ ID NO: 2 which comprises the gene having the nucleotide sequence shown by SEQ ID NO: 1 (hereinafter referred to as FDC1 gene) as the open reading frame was determined. The protein encoded by FDC1 gene which is presumed from the determined nucleotide sequence consists of 503 amino acid residues. This nucleotide sequence shown by SEQ ID NO: 1 was found to be identical with the sequence located at 1512140–1513651 on the sequence of chromosome No. IV among the nucleotide sequences published by the yeast genome project [e.g. Internet http://genome-www.stanford.edu/sacchdb/]. Simple homology analysis was made on FDC1 gene, FDC gene of *Bacillus pumilus* [Appl. Environ. Microbiol., 61, 4484–4486 (1995)] and the gene encoding phenylacrylic acid decarboxylase of *Saccharomyces cerevisiae* (hereinafter referred to as PAD1 gene) [Gene, 142, 107–112 (1994)] using DNASIS ver 3.0 (Hitachi Software Engineering Co., Ltd.). As a result, FDC1 gene showed only 30% and 41% homology to the above two genes, respectively, with respect to the entire nucleotide sequence, and only 11.25% and 10.37% homology with respect to the entire amino acid sequence translated from the nucleotide sequence. Further, homology search by BLAST method [e.g. Utilization of Data Base on Genome Net, Kyoritsu Shuppan Co., Ltd. (1996)] revealed that FDC1 gene did not show significant homology to either of FDC gene of *Bacillus pumilus* and PAD1 gene.

Example 2

Figure 2:
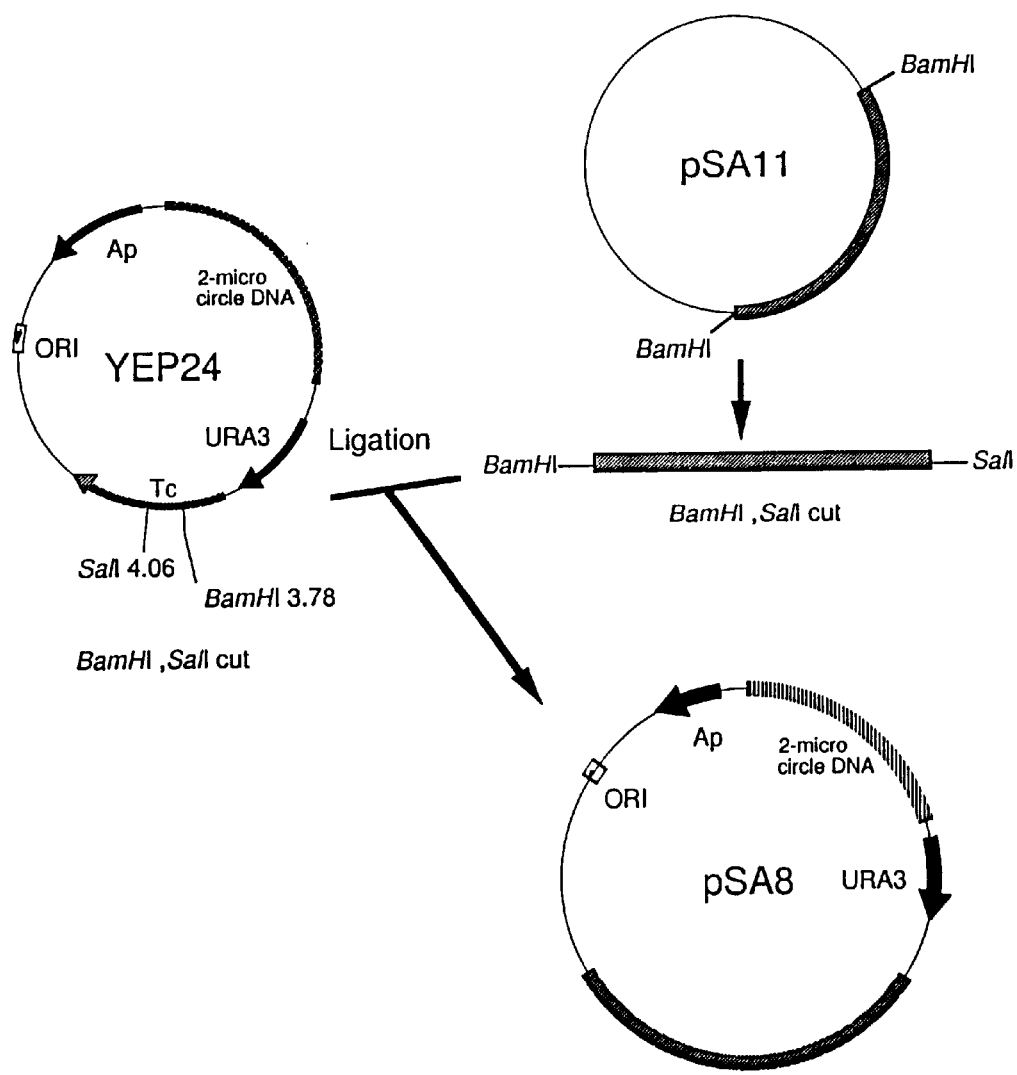
FIG. 2 illustrates the steps for constructing the plasmid for the expression of FDC1 gene of FIG. 1.

Preparation of Shochu Yeast Conferred with Ferulic Acid Decarboxylase Activity (1) Construction of plasmid for FDC1 gene expression About 5 μg of pSA11 plasmid DNA was dissolved in 20 μl of H buffer [50 mM Tris hydrochloride buffer (pH 7.5), 10 mM magnesium chloride, 1 mm dithiothreitol, and 100 mM sodium chloride], and 10 units each of restriction enzymes BamHI and SalI were added thereto. Reaction was carried out overnight at 37° C., followed by separation of the reaction product by 0.8% agarose gel electrophoresis. The segment of the gel containing the band of the DNA fragment of about 3.6 kbp was cut out, and the fragment was extracted and purified by using GENECLEAN II Kit (Bio 101 Co., Ltd.). The same procedure as above was repeated except that yeast-*E. coli* shuttle vector YEp24 was used in place of plasmid pSA11, whereby a DNA fragment of about 7.7 kbp was extracted and purified. The DNA fragment of about 3.6 kbp derived from plasmid pSA11 (1 μg) and the DNA fragment of about 7.7 kbp derived from YEp24 (0.1 μg) were subjected to ligation reaction overnight at 16° C. using Ligation Kit (Takara Shuzo Co., Ltd.). The reaction mixture (5 μl) was used for transformation of competent *E. coli* JM109 strain (Toyobo Co., Ltd.). The obtained transformants were smeared on ampicillin LB agar medium [1% Bacto-tryptone (Difco Laboratories Inc.), 0.5% yeast extract, 1% sodium chloride, 1.5% agar, and 50 μg/ml ampicillin] and cultured at 37° C. for 20 hours. After the completion of culturing, the formed colonies were isolated and cultured, and plasmid DNAs were extracted and purified from the cultures. The obtained plasmids were cleaved with restriction enzymes BamHI and SalI, and one of them was found to have the DNA fragment of about 3.6 kbp and was designated expression plasmid pSA8 (FIG. 2).

(2) Introduction of FDC1 gene into shochu yeast and its expression

K9H14-3u strain was inoculated into 100 ml of YPD medium in an Erlenmeyer flask, and cultured with shaking at 30° C. until the cell density reached $2-4 \times 10^7$ cells/ml. After the completion of culturing, the cells were collected by centrifugation (2500 rpm, 5 minutes) and then brought into contact with plasmid pSA8 by the lithium acetate method. K9H14-3u strain contacted with plasmid pSA8 was inoculated on SD agar medium (0.67% Yeast Nitrogen Base w/o Amino Acid, 2% glucose, and 2% agar), and cultured at 30° C. for 2–5 days. After the completion of culturing, YSA7 strain was obtained from one of the formed colonies as a transformant in which the uracil-requirement of K9H14-3u strain was complemented.

YSA7 strain, K9H14 strain and K9H14-C strain were respectively inoculated into YPD medium, and cultured overnight at 30° C. To 0.9 ml of each of the resulting cultures was added 0.1 ml of 1 g/l ferulic acid solution, followed by static culture at 25° C. for 22 hours. After the completion of culturing, the 4-vinylguaiacol content of the culture supernatant was determined by high performance liquid chromatography. The formation of 4-vinylguaiacol was confirmed in the culture of YSA7 strain, whereas the formation of 4-vinylguaiacol was little observed in the cultures of K9H14 strain and K9H14-C strain.

Example 3

Production of Rice Shochu

Rice shochu was produced by small scale brewing using YSA7 strain, K9H14 strain and K9H14-C strain, and 840 g of total rice. The proportion of raw materials is shown in Table 2.

TABLE 2

|  | 1st addition | 2nd addition | Total |
|---|---|---|---|
| Total rice (g) | 280 | 560 | 840 |
| Steamed rice (g) | 280 | — | 280 |
| Rice koji (g) | — | 560 | 560 |
| Water (ml) | 400 | 800 | 1200 |

After the second addition of the materials, alcohol fermentation was carried out at 20° C. for 10 days, and the resulting moromi was distilled to obtain rice shochu.

The produced shochu was analyzed according to the official analytical methods of the National Tax Administration Agency of Japan. The ethanol content and the 4-vinylguaiacol content of each shochu obtained were determined by high performance liquid chromatography, and sensory evaluation was made by 7 panelists.

The results are shown in Table 3. The results of the sensory evaluation are expressed by the average points of the 7 panelists.

TABLE 3

|  | YSA7 strain | K9H14 strain | K9H14-C strain |
|---|---|---|---|
| Ethanol (%) | 34.6 | 34.6 | 34.6 |
| 4VG (ppm) | 2.0 | 0.8 | 0.8 |
| Sensory evaluation* | 2.5 | 3.0 | 3.0 |

*Evaluation in 5 points (1:good, 5:bad)

As shown in Table 3, rice shochu produced using YSA7 strain had a significantly higher 4-vinylguaiacol content as compared with that produced using its parent strain, K9H14 strain, and was also found to have a characteristic flavor by the sensory evaluation.

What is claimed is:

1. A distilled liquor obtainable by a process which comprises adding to moromi an enzyme source having ferulic acid decarboxylase activity which is derived from the transformant carrying the recombinant vector which comprises the gene encoding the protein which is selected from the group consisting of:

(a) a protein having the amino acid sequence encoded by SEQ ID NO: 1; and (b) a protein having ferulic acid decarboxylase activity and having an amino acid sequence wherein one or more amino acid residues are deleted, substituted or added in the amino acid sequence represented by SEQ ID NO: 1.

2. A distilled liquor obtainable by a process which is characterized in that a yeast having an enhanced ferulic acid decarboxylase activity is used.

* * * * *

UNITED STATES PATENT AND TRADEMARK OFFICE
CERTIFICATE OF CORRECTION

PATENT NO. : 5,955,137

DATED : September 21, 1999

INVENTOR(S) : SHOJI AGO ET AL.

Page 1 of 2

It is certified that error appears in the above-identified patent and that said Letters Patent is hereby corrected as shown below:

ON THE TITLE PAGE [56] References Cited:

PUBLICATIONS, after "Rosazza et al.", "Review" should read --"Review:--; and insert --Zago, A. et al, "Cloning, sequencing, and expression in Escherichia coli of the Bacillus punilus gene for ferulic acid decarboxylase," Applied and Environmental Microbiology (Dec. 1995), Vol. 61, no. 12, pp. 4484-4486.--; and FOREIGN PATENT DOCUMENTS, insert
--FOREIGN PATENT DOCUMENTS
7-115957 5/1995 Japan.--

COLUMN 3:

Line 26, "enzyme" should read --enzymes--.

COLUMN 4:

Line 23, "arbitrary" should read --an arbitrary--; and
Line 35, "a" should be deleted.

COLUMN 5:

Line 19, "trp" should read --trp--;
Line 21, "(Ptrp), lac promoter (Plac)," should read --(Ptrp), lac promoter (Plac),--;
Line 22, "Ptrps" should read --Ptrps--;
Line 23, "(Ptrpx2) and tac" should read --(Ptrpx2) and tac--; and
Line 42 "MFα11" should read --MFα1--.

UNITED STATES PATENT AND TRADEMARK OFFICE
CERTIFICATE OF CORRECTION

PATENT NO. : 5,955,137

DATED : September 21, 1999

INVENTOR(S) : SHOJI AGO ET AL.

It is certified that error appears in the above-identified patent and that said Letters Patent is hereby corrected as shown below:

<u>COLUMN 6</u>:

Line 60, "lac" should read --<u>lac</u>--; and
    Line 63, "trp" should read --<u>trp</u>--.

Signed and Sealed this

Fourth Day of July, 2000

Attest:

Attesting Officer

Q. TODD DICKINSON

Director of Patents and Trademarks

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
    (A) LENGTH:  1512 bases
    (B) TYPE: nucleic acid
    (C) STRANDEDNESS: single
    (D) TOPOLOGY: linear (ii) MOLECULE TYPE: Genomic DNA (vi) ORIGINAL SOURCE:
    (A) ORGANISM: Saccharomyces cerevisiae
    (B) STRAIN: YSA7

(ix) FEATURE:
    (A) NAME/KEY: CDS
    (B) LOCATION: 1 to 1512
    (C) IDENTIFICATION METHOD: E (xi) SEQUENCE DESCRIPTION: SEQ ID NO:  1:

```
ATG AGG AAG CTA AAT CCA GCT TTA GAA TTT AGA GAC TTT ATC CAG GTC        48
Met Arg Lys Leu Asn Pro Ala Leu Glu Phe Arg Asp Phe Ile Gln Val
 1               5                  10                  15

TTA AAA GAT GAA GAT GAC TTA ATC GAA ATT ACC GAA GAG ATT GAT CCA        96
Leu Lys Asp Glu Asp Asp Leu Ile Glu Ile Thr Glu Glu Ile Asp Pro
             20                  25                  30
```

| | | |
|---|---|---|
| AAT CTC GAA GTA GGT GCA ATT ATG AGG AAG GCC TAT GAA TCC CAC TTA<br>Asn Leu Glu Val Gly Ala Ile Met Arg Lys Ala Tyr Glu Ser His Leu<br>35 40 45 | 144 | |
| CCA GCC CCG TTA TTT AAA AAT CTC AAA GGT GCT TCG AAG GAT CTT TTC<br>Pro Ala Pro Leu Phe Lys Asn Leu Lys Gly Ala Ser Lys Asp Leu Phe<br>50 55 60 | 192 | |
| AGC ATT TTA GGT TGC CCA GCC GGT TTG AGA AGT AAG GAG AAA GGA GAT<br>Ser Ile Leu Gly Cys Pro Ala Gly Leu Arg Ser Lys Glu Lys Gly Asp<br>65 70 75 80 | 240 | |
| CAT GGT AGA ATT GCC CAT CAT CTG GGG CTC GAC CCA AAA ACA ACT ATC<br>His Gly Arg Ile Ala His His Leu Gly Leu Asp Pro Lys Thr Thr Ile<br>85 90 95 | 288 | |
| AAG GAA ATC ATA GAT TAT TTG CTG GAG TGT AAG GAG AAG GAA CCT CTC<br>Lys Glu Ile Ile Asp Tyr Leu Leu Glu Cys Lys Glu Lys Glu Pro Leu<br>100 105 110 | 336 | |
| CCC CCA ATC ACT GTT CCT GTG TCA TCT GCA CCT TGT AAA ACA CAT ATA<br>Pro Pro Ile Thr Val Pro Val Ser Ser Ala Pro Cys Lys Thr His Ile<br>115 120 125 | 384 | |
| CTT TCT GAA GAA AAA ATA CAT CTA CAA AGC CTG CCA ACA CCA TAT CTA<br>Leu Ser Glu Glu Lys Ile His Leu Gln Ser Leu Pro Thr Pro Tyr Leu<br>130 135 140 | 432 | |
| CAT GTT TCA GAC GGT GGC AAG TAC TTA CAA ACG TAC GGA ATG TGG ATT<br>His Val Ser Asp Gly Gly Lys Tyr Leu Gln Thr Tyr Gly Met Trp Ile<br>145 150 155 160 | 480 | |
| CTT CAA ACT CCA GAT AAA AAA TGG ACT AAT TGG TCA ATT GCT AGA GGT<br>Leu Gln Thr Pro Asp Lys Lys Trp Thr Asn Trp Ser Ile Ala Arg Gly<br>165 170 175 | 528 | |
| ATG GTT GTA GAT GAC AAG CAT ATC ACT GGT CTG GTA ATT AAA CCA CAA<br>Met Val Val Asp Asp Lys His Ile Thr Gly Leu Val Ile Lys Pro Gln<br>180 185 190 | 576 | |
| CAT ATT AGA CAA ATT GCT GAC TCT TGG GCA GCA ATT GGA AAA GCA AAT<br>His Ile Arg Gln Ile Ala Asp Ser Trp Ala Ala Ile Gly Lys Ala Asn<br>195 200 205 | 624 | |
| GAA ATT CCT TTC GCG TTA TGT TTT GGC GTT CCC CCA GCA GCT ATT TTA<br>Glu Ile Pro Phe Ala Leu Cys Phe Gly Val Pro Pro Ala Ala Ile Leu<br>210 215 220 | 672 | |
| GTT AGT TCC ATG CCA ATT CCT GAA GGT GTT TCT GAA TCG GAT TAT GTT<br>Val Ser Ser Met Pro Ile Pro Glu Gly Val Ser Glu Ser Asp Tyr Val<br>225 230 235 240 | 720 | |
| GGC GCA ATC TTG GGT GAG TCG GTT CCA GTA GTA AAA TGT GAG ACC AAC<br>Gly Ala Ile Leu Gly Glu Ser Val Pro Val Val Lys Cys Glu Thr Asn<br>245 250 255 | 768 | |
| GAT TTA ATG GTT CCT GCA ACG AGT GAG ATG GTA TTT GAG GGT ACT TTG<br>Asp Leu Met Val Pro Ala Thr Ser Glu Met Val Phe Glu Gly Thr Leu<br>260 265 270 | 816 | |
| TCC TTA ACA GAT ACA CAT CTG GAA GGC CCA TTT GGT GAG ATG CAT GGA<br>Ser Leu Thr Asp Thr His Leu Glu Gly Pro Phe Gly Glu Met His Gly<br>275 280 285 | 864 | |
| TAT GTT TTC AAA AGC CAA GGT CAT CCT TGT CCA TTG TAC ACT GTC AAG<br>Tyr Val Phe Lys Ser Gln Gly His Pro Cys Pro Leu Tyr Thr Val Lys<br>290 295 300 | 912 | |
| GCT ATG AGT TAC AGA GAC AAT GCT ATT CTA CCT GTT TCG AAC CCC GGT<br>Ala Met Ser Tyr Arg Asp Asn Ala Ile Leu Pro Val Ser Asn Pro Gly<br>305 310 315 320 | 960 | |
| CTT TGT ACG GAT GAG ACA CAT ACC TTG ATT GGT TCA CTA GTG GCT ACT<br>Leu Cys Thr Asp Glu Thr His Thr Leu Ile Gly Ser Leu Val Ala Thr<br>325 330 335 | 1008 | |
| GAG GCC AAG GAG CTG GCT ATT GAA TCT GGC TTG CCA ATT CTG GAT GCC<br>Glu Ala Lys Glu Leu Ala Ile Glu Ser Gly Leu Pro Ile Leu Asp Ala<br>340 345 350 | 1056 | |

-continued

```
TTT ATG CCT TAT GAG GCT CAG GCT CTT TGG CTT ATC TTA AAG GTG GAT        1104
Phe Met Pro Tyr Glu Ala Gln Ala Leu Trp Leu Ile Leu Lys Val Asp
    355                 360                 365

TTG AAA GGG CTG CAA GCA TTG AAG ACA ACG CCT GAA GAA TTT TGT AAG        1152
Leu Lys Gly Leu Gln Ala Leu Lys Thr Thr Pro Glu Glu Phe Cys Lys
370                 375                 380

AAG GTA GGT GAT ATT TAC TTT AGG ACA AAA GTT GGT TTT ATA GTC CAT        1200
Lys Val Gly Asp Ile Tyr Phe Arg Thr Lys Val Gly Phe Ile Val His
385                 390                 395                 400

GAA ATA ATT TTG GTG GCA GAT GAT ATC GAC ATA TTT AAC TTC AAA GAA        1248
Glu Ile Ile Leu Val Ala Asp Asp Ile Asp Ile Phe Asn Phe Lys Glu
            405                 410                 415

GTC ATC TGG GCC TAC GTT ACA AGA CAT ACA CCT GTT GCA GAT CAG ATG        1296
Val Ile Trp Ala Tyr Val Thr Arg His Thr Pro Val Ala Asp Gln Met
        420                 425                 430

GCT TTT GAT GAT GTC ACT TCT TTT CCT TTG GCT CCC TTT GTT TCG CAG        1344
Ala Phe Asp Asp Val Thr Ser Phe Pro Leu Ala Pro Phe Val Ser Gln
    435                 440                 445

TCA TCC AGA AGT AAG ACT ATG AAA GGT GGA AAG TGC GTT ACT AAT TGC        1392
Ser Ser Arg Ser Lys Thr Met Lys Gly Gly Lys Cys Val Thr Asn Cys
450                 455                 460

ATA TTT AGA CAG CAA TAT GAG CGC AGT TTT GAC TAC ATA ACT TGT AAT        1440
Ile Phe Arg Gln Gln Tyr Glu Arg Ser Phe Asp Tyr Ile Thr Cys Asn
465                 470                 475                 480

TTT GAA AAG GGA TAT CCA AAA GGA TTA GTT GAC AAA GTA AAT GAA AAT        1488
Phe Glu Lys Gly Tyr Pro Lys Gly Leu Val Asp Lys Val Asn Glu Asn
            485                 490                 495

TGG AAA AGG TAC GGA TAT AAA TAA                                        1512
Trp Lys Arg Tyr Gly Tyr Lys
            500
```

(2) INFORMATION FOR SEQ ID NO: 2:

(i) SEQUENCE CHARACTERISTICS:
        (A) LENGTH: 3930
        (B) TYPE: nucleic acid
        (C) STRANDEDNESS: single
        (D) TOPOLOGY: linear (ii) MOLECULE TYPE: Genomic DNA (vi) ORIGINAL SOURCE:
        (A) ORGANISM: Saccharomyces cerevisiae
        (B) STRAIN: YSA7

(ix) FEATURE:
        (A) NAME/KEY: CDS
        (B) LOCATION: 532 to 2043
        (C) IDENTIFICATION METHOD: E (ix) FEATURE:
        (A) NAME/KEY: cleavage-site
        (B) LOCATION: 1 to 6, 3923 to 3930
        (C) IDENTIFICATION METHOD: S
        (D) OTHER INFORMATION: BamHI cleavage-site (ix) FEATURE:
        (A) NAME/KEY: cleavage-site
        (B) LOCATION: 656 to 661
        (C) IDENTIFICATION METHOD: S
        (D) OTHER INFORMATION: StuI cleavage-site (ix) FEATURE:
        (A) NAME/KEY: cleavage-site
        (B) LOCATION: 1527 to 1732
        (C) IDENTIFICATION METHOD: S
        (D) OTHER INFORMATION: SpeI cleavage-site (ix) FEATURE:
        (A) NAME/KEY: cleavage-site (B) LOCATION: 3555 to 3600
(C) IDENTIFICATION METHOD: S
(D) OTHER INFORMATION: SalI cleavage-site (xi) SEQUENCE DESCRIPTION: SEQ ID NO: 2:

```
GGATCCTAGA CTGCTTTGGC ATCCACGCTG ACACTTTTCC TCGTTGGGAA GGAATAAAAA      60

GCAAGTAACA CTTTTTCTGA GCATTTTATT ACGTTACTCA ACTACTAATA GAGTTGATTT     120

GTTACTTGCT AAAATCTTTT TATATTTCTT TTAGCCCCGA CAGAACTTGT TGCAAATGAA     180

TACAAACCGT GAACTTCCCG ATATCATTCT AATTGAACCC AGATATTTAC ACATGTACTT     240

CTTACTCATT TTCAATGTCA GCTTAAATAT CGTCTAAAAC AATATTTTAC TAGATACGCA     300

GTTCAATCTT CGCGCATATT TTCACGAAAG TCCAAATTGC GTACGTAGTT TTATGTCAAA     360

GTGACCGCCG TTGTAGCGTA CTTTTTCCTA TAAGACAAGC TCGTGATATC AGGAATATAT     420

CAGGAATGTA AACGAATACC GCATATCTTT TTGATTTTTT TCCTCTGAGT TATTCTATTC     480

TTGACATTAT TACATCACCA ATTCAAAGA ATTGTCAATT TATATATTTA AATGAGGAAG      540

CTAAATCCAG CTTTAGAATT TAGAGACTTT ATCCAGGTCT TAAAAGATGA AGATGACTTA     600

ATCGAAATTA CCGAAGAGAT TGATCCAAAT CTCGAAGTAG GTGCAATTAT GAGGAAGGCC     660

TATGAATCCC ACTTACCAGC CCCGTTATTT AAAAATCTCA AGGTGCTTC GAAGGATCTT      720

TTCAGCATTT TAGGTTGCCC AGCCGGTTTG AGAAGTAAGG AGAAAGGAGA TCATGGTAGA     780

ATTGCCCATC ATCTGGGGCT CGACCCAAAA ACAACTATCA AGGAAATCAT AGATTATTTG     840

CTGGAGTGTA AGGAGAAGGA ACCTCTCCCC CCAATCACTG TTCCTGTGTC ATCTGCACCT     900

TGTAAAACAC ATATACTTTC TGAAGAAAAA ATACATCTAC AAAGCCTGCC AACACCATAT     960

CTACATGTTT CAGACGGTGG CAAGTACTTA CAAACGTACG GAATGTGGAT TCTTCAAACT    1020

CCAGATAAAA AATGGACTAA TTGGTCAATT GCTAGAGGTA TGGTTGTAGA TGACAAGCAT    1080

ATCACTGGTC TGGTAATTAA ACCACAACAT ATTAGACAAA TTGCTGACTC TTGGGCAGCA    1140

ATTGGAAAAG CAAATGAAAT TCCTTTCGCG TTATGTTTTG GCGTTCCCCC AGCAGCTATT    1200

TTAGTTAGTT CCATGCCAAT TCCTGAAGGT GTTTCTGAAT CGGATTATGT TGGCGCAATC    1260

TTGGGTGAGT CGGTTCCAGT AGTAAAATGT GAGACCAACG ATTTAATGGT TCCTGCAACG    1320

AGTGAGATGG TATTTGAGGG TACTTTGTCC TTAACAGATA CACATCTGGA AGGCCCATTT    1380

GGTGAGATGC ATGGATATGT TTTCAAAAGC CAAGGTCATC CTTGTCCATT GTACACTGTC    1440

AAGGCTATGA GTTACAGAGA CAATGCTATT CTACCTGTTT CGAACCCCGG TCTTTGTACG    1500

GATGAGACAC ATACCTTGAT TGGTTCACTA GTGGCTACTG AGGCCAAGGA GCTGGCTATT    1560

GAATCTGGCT TGCCAATTCT GGATGCCTTT ATGCCTTATG AGGCTCAGGC TCTTTGGCTT    1620

ATCTTAAAGG TGGATTTGAA AGGGCTGCAA GCATTGAAGA CAACGCCTGA AGAATTTTGT    1680

AAGAAGGTAG GTGATATTTA CTTTAGGACA AAAGTTGGTT TTATAGTCCA TGAAATAATT    1740

TTGGTGGCAG ATGATATCGA CATATTTAAC TTCAAAGAAG TCATCTGGGC CTACGTTACA    1800

AGACATACAC CTGTTGCAGA TCAGATGGCT TTTGATGATG TCACTTCTTT TCCTTTGGCT    1860

CCCTTTGTTT CGCAGTCATC CAGAAGTAAG ACTATGAAAG GTGGAAAGTG CGTTACTAAT    1920

TGCATATTTA GACAGCAATA TGAGCGCAGT TTTGACTACA TAACTTGTAA TTTTGAAAAG    1980

GGATATCCAA AAGGATTAGT TGACAAAGTA AATGAAAATT GGAAAAGGTA CGGATATAAA    2040

TAATTGCCAT AGACTTTCTA CGGAAGAAAA ACCATATAAT CAGATTTTAA ATAAAATTTT    2100

CCGAACTTTT ATACTCCACG GTTTTGGAGT TGTTTGATTG CAGTGACAAG CAGTGCGCCA    2160

TTAACACTAT CCATCTTTCG TACAAAGTAA AGATAAAGTT ATTTTCCTGA GGTGAGAACC    2220
```

-continued

```
GTAAATCTTT ATAGACAAGG AGTATTTATA ACTAAACTAT TACCTTGTTA CTTATGGAAT    2280

TAATCTTGAC TAATAGGCAG ATGATCAACA GTTATTGATT TTGAGTGAAA GTCCATAAAG    2340

TTACAGTATG TAATTACAGT ACGTAATTAA GGAATGTCTG TAAATATATG CTCCTTTTTT    2400

TTTTTCCACT TACTATGATT TTAGTAAAGC ACCATGATGA TGTAGATGCG TAATACTCTA    2460

TAAATGTAAC ATCGTTAAAG CATTGGTTAT TTTAATTTCA TTCTATAAAC CAATATTTCT    2520

GACAGCACAT AAAAAATAAA TGGACTATAT TAACAGCAAA TATCGGTTAA TCTAGGGCAT    2580

AATTATTTAA CATCAAAAAG AAAGTTGCTA GTTGTTCTAG TATTGCTCGG AGTACCTCAA    2640

ACGGTAAAAA GATAATATTT GTTTCCGCTT TTATCATTGA ATAGCTTAGA AATTCTCTCC    2700

CTAGCGACCA TTTAAGGAAT GTAGCTAACA AAAATGATTC AAGTATGTTG CTCCTAAGCA    2760

GATATGTACT CTATAAGTTG AATCACTATA TCATTGAAAT ATAGTGGCGA GGGCGTACAT    2820

AAAATCAAAG GAACTATGCA ATAGACTCAA TTAAATGCCA CATAGCTATT TAAGACTCCA    2880

AATCTCCAAT ACAATCATTC GTTAAAGATT TTTTGTATTC TGCTGATATC TTTTTCTACA    2940

GTTTCTTGAG TGTCTAGTGA TTGCATAAAA TGACCACAGT ATTTTTAGTA CTCATGGCCT    3000

GTATGCAATT GCAAGGAACG GTATTACTTT TACAAAAACC CTGCTTTCCG GCAAGTTCAG    3060

CTGTCATTTG GTAAGATTTT GAAAATAGTG GAAACAATGG ATTATCAACG AATAGTCTTT    3120

AAACATAAGT GCTAAAATTC AAAACATCAT TTGATGCGTG CGGTGCATTT TTTCGTGCTG    3180

AATGAACTTT TGGAGATATC TGCCTTCGCC AATGAATATG CATTACCATT AATTGCATAG    3240

TAACCGTATA CATGAAAATG GAAATAATGA ACTGATTATT AAAAATAGCT AATGCAGGTG    3300

GGATTTGAGA CATTGTGGTT ATCCTGTCAG CCTGTATTTT GCGCTTTAAG GTATTTCATA    3360

AAAGTTAGAA TAAAATTTAA AAGTTCCATT CTATGAAACT GTAATTATAG GTATATACTA    3420

TCATCTACCA ATCTTACCCA TGTATAGTTC TAATATTAAA GACAGAGTAG GTAAAAAAAA    3480

AAATGGTAAT CAAAACGTGA TCGCTTATAT TCGGTATGGA CAAGCTTTGA ATATTCCCTA    3540

GAAAATGCAA TAGTATGTCA TAATGAAAGA AGATTGTAAT ACAATGCTTG GAATGTCGAC    3600

CGGCAGAAAC CCGTGTCACA TGGCCTTATT CAACGTGACG TTGTGATATA TGTAGAACAT    3660

GCTTTAGATG AGGCGGTATT TGACTGTAGC ATCTTCTAAA ATGTGCTGAT ATTGTTAAAT    3720

CTCAATCAAA CTGAGAGAGT ATGAGAGACT GAAAAAGTGG GATTCTGCCT GTGGTGCTAA    3780

TATCCTTAAA ATGCTAAACT GAAAGAAGTA ATATAATCAT ATATATTGAT CATGTATCAT    3840

ACAAAAGATG CATGTATTTT AGTAATATTA ACTGCTACTA TGATGTAGTA GACGATCGAT    3900

AATCGAATCT TGCGGTATAT TCTAGGATCC                                     3930
```